United States Patent
Lee et al.

(10) Patent No.: US 10,179,752 B2
(45) Date of Patent: *Jan. 15, 2019

(54) 1-OCTENE COMPOSITION

(71) Applicant: LG CHEM, LTD., Seoul (KR)

(72) Inventors: Yong Ho Lee, Daejeon (KR); Seok Pil Sa, Daejeon (KR); Eun Ji Shin, Daejeon (KR); Ki Soo Lee, Daejeon (KR); Jin Young Park, Daejeon (KR); Seul Ki Im, Daejeon (KR); Yoon Ki Hong, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/941,708

(22) Filed: Mar. 30, 2018

(65) Prior Publication Data

US 2018/0222816 A1 Aug. 9, 2018

Related U.S. Application Data

(63) Continuation of application No. 14/915,553, filed as application No. PCT/KR2015/009739 on Sep. 16, 2015, now Pat. No. 9,969,659.

(30) Foreign Application Priority Data

Jun. 1, 2015 (KR) .................. 10-2015-0077366
Sep. 4, 2015 (KR) .................. 10-2015-0125688

(51) Int. Cl.
*C07C 2/42* (2006.01)
*C07C 13/10* (2006.01)
(Continued)

(52) U.S. Cl.
CPC ............... *C07C 2/42* (2013.01); *B01J 31/188* (2013.01); *C07C 2/32* (2013.01); *C07C 13/10* (2013.01);
(Continued)

(58) Field of Classification Search
CPC .. C07C 2/32; C07C 11/02; C07C 2/42; C07C 13/11; C07C 13/10; C07C 13/12;
(Continued)

(56) References Cited

U.S. PATENT DOCUMENTS 3,257,367 A 6/1966 Haven, Jr.
4,985,184 A 1/1991 Takahashi et al.
(Continued)

FOREIGN PATENT DOCUMENTS

JP 08277307 A 10/1996
JP 2003511493 A 3/2003
(Continued)

OTHER PUBLICATIONS

Carter, A. et al., "High activity ethylene trimerisation catalysts based on diphosphine ligands", Chem. Commun., 2002, 858.
(Continued)

*Primary Examiner* — Pamela H Weiss
(74) *Attorney, Agent, or Firm* — Dentons US LLP

(57) ABSTRACT

The present invention relates to a 1-octene composition. The 1-octene composition according to the present invention is prepared by ethylene oligomerization and comprises a high content of 1-octene and monomers useful for copolymerization of 1-octene at the same time.

4 Claims, 1 Drawing Sheet

(51) Int. Cl.
*C07C 13/11* (2006.01)
*B01J 31/18* (2006.01)
*C07C 13/12* (2006.01)
*C07C 2/32* (2006.01)

(52) U.S. Cl.
CPC .............. *C07C 13/11* (2013.01); *C07C 13/12* (2013.01); *B01J 2231/20* (2013.01); *B01J 2531/62* (2013.01); *C07C 2531/18* (2013.01); *C07C 2601/08* (2017.05); *C07C 2601/10* (2017.05); *Y02P 20/52* (2015.11)

(58) Field of Classification Search
CPC ............ C07C 2101/10; C07C 2601/10; C07C 2601/08; C07C 2101/08; C07C 2531/18; B01J 31/188; B01J 2531/62; B01J 2231/20
See application file for complete search history.

(56) References Cited

U.S. PATENT DOCUMENTS

| | | | |
|---|---|---|---|
| 9,409,833 | B2 | 8/2016 | Shin et al. |
| 9,701,699 | B2 | 7/2017 | Lee et al. |
| 9,802,874 | B2 | 10/2017 | Han et al. |
| 9,969,659 | B2 * | 5/2018 | Lee .................... C07C 13/12 |
| 2006/0229480 | A1 | 10/2006 | Blann et al. |
| 2007/0185363 | A1 | 8/2007 | Bercaw et al. |
| 2007/0232481 | A1 | 10/2007 | Zhang et al. |
| 2008/0027188 | A1 | 1/2008 | Small et al. |
| 2010/0081777 | A1 | 4/2010 | Gao et al. |
| 2010/0137669 | A1 | 6/2010 | Han et al. |
| 2010/0145124 | A1 * | 6/2010 | Han .................... B01J 31/24 585/528 |
| 2010/0179295 | A1 | 7/2010 | Yasuda et al. |
| 2010/0298618 | A1 | 11/2010 | Aliyev et al. |
| 2011/0028654 | A1 | 2/2011 | Sita et al. |
| 2011/0086991 | A1 | 4/2011 | Dixon et al. |
| 2012/0130086 | A1 * | 5/2012 | Han .................... C07C 2/36 548/402 |
| 2012/0172645 | A1 | 7/2012 | Sydora |
| 2012/0220728 | A1 | 8/2012 | Uekusa et al. |
| 2015/0045603 | A1 | 2/2015 | Han et al. |
| 2015/0275127 | A1 | 10/2015 | Patil et al. |
| 2016/0122371 | A1 | 5/2016 | Lee et al. |
| 2016/0207946 | A1 | 7/2016 | Shin et al. |

FOREIGN PATENT DOCUMENTS

| | | |
|---|---|---|
| JP | 2014511912 A | 5/2014 |
| JP | 5623912 B2 | 11/2014 |
| KR | 1020010074920 A | 8/2001 |
| KR | 100417037 B1 | 1/2004 |
| KR | 1020040065110 A | 7/2004 |
| KR | 100851768 B1 | 8/2008 |
| KR | 1020100087913 A | 8/2010 |
| KR | 101065596 B1 | 9/2011 |
| KR | 1020130105126 A | 9/2013 |
| KR | 1020130142151 A | 12/2013 |
| KR | 1020150058034 A | 5/2015 |
| KR | 1020150058049 A | 5/2015 |

OTHER PUBLICATIONS

Overett, Matthew J. et al., "Mechanistic Investigations of the Ethylene Tetramerisation Reaction", J. Am. Chem. Soc. 2005, 127, 10723-10730.

McGuinness, D. S., "Olefin Oligomerization via Metallacycles: Dimerization, Trimerization, Tetramerization, and Beyond", Chem. Rev. 2011, 111, 2321-2341.

van Leeuwen, Piet W. N. M., et al. "New processes for the selective production of 1-octene", Coordination Chemistry Reviews, 255, (2011) 1499-1517.

* cited by examiner

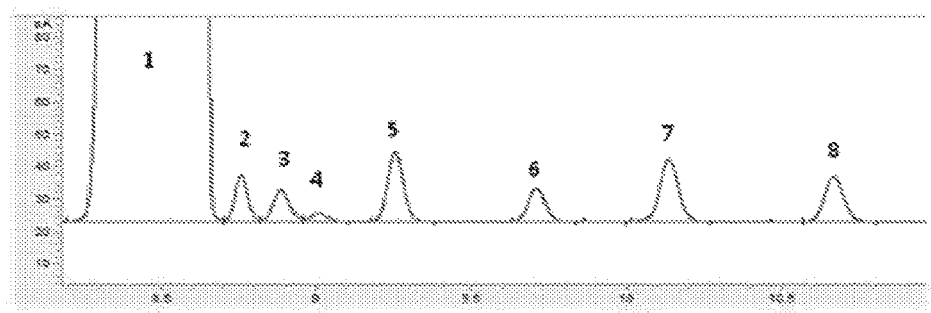

1-OCTENE COMPOSITION

CROSS-REFERENCE TO RELATED APPLICATION(S)

This application is continuation application of and claims priority to U.S. patent application Ser. No. 14/915,553, filed Feb. 29, 2016, which is a National Stage Application of International Application No. PCT/KR2015/009739, filed Sep. 16, 2015, and claims the benefit of Korean Patent Application No. 10-2015-0077366 on Jun. 1, 2015, and Korean Patent Application No. 10-2015-0125688 filed Sep. 4, 2015, the contents of which are incorporated by reference in their entirety for all purposes as if fully set forth below.

TECHNICAL FIELD

The present invention relates to a 1-octene composition which is prepared by ethylene oligomerization and comprises a high content of 1-octene and monomers useful for copolymerization of 1-octene at the same time.

BACKGROUND OF ART

Linear alpha-olefin is widely used in important commercial substances such as comonomers, detergents, lubricants, plasticizers or the like, and in particular, 1-hexene and 1-octene are commonly used as comonomers for controlling density of polyethylene during preparation of linear low density polyethylene (LLDPE).

In the conventional preparation process of LLDPE (Linear Low-Density Polyethylene), copolymerization of ethylene with alpha-olefin, for example, a comonomer such as 1-hexene and 1-octene is carried out in order to control density by forming branches in the polymer backbone.

Therefore, there is a problem that the production cost of LLDPE having a high content of comonomers is high. Various methods have been tried to solve this problem.

Further, because the application field or market size depends on the type of alpha-olefin, a technique capable of selectively producing a particular olefin is commercially important. Recently, many studies have been conducted on chromium catalysts for preparing 1-hexene or 1-octene with a high selectivity through selective ethylene oligomerization.

The conventional commercial methods for preparation of 1-hexene or 1-octene are the SHOP process of Shell Chemical, and the Ziegler Process of Chevron Philips, which are used to produce alpha-olefins with a wide distribution ranging from 4 to 20 carbons.

A chromium-based catalyst for ethylene trimerization having a ligand of the formula (R1)(R2)X—Y—X(R3)(R4) has been suggested, in which X is phosphorus, arsenic or antimony, Y is a linking group such as —N(R5)-, and at least one of R1, R2, R3 and R4 has a polar substituent or an electron donating substituent.

Further, studies have been conducted on (o-ethylphenyl)$_2$PN(Me)P(o-ethylphenyl)$_2$ as a ligand which shows no catalytic activity for 1-hexene under catalytic conditions and has no polar substituent in at least one of R1, R2, R3 and R4 (*Chem. Commun.*, 2002, 858).

However, the prior ligands containing heteroatoms as described above are still required to maintain their polymerization activity consistently during reactions for producing 1-octene or 1-hexene and to have high selectivity.

Meanwhile, it is required to minimize production of by-products other than 1-octene to obtain pure 1-octene upon preparation of 1-octene by olefin oligomerization. However, production of by-products other than 1-octene is unavoidable in practice. Since the kind and content of by-products vary depending on the oligomerization catalyst, catalysts with high 1-octene selectivity must be used. However, some by-products may be incorporated in the polyolefin during polymerization and may result in improvement of physical properties. In this case, there is no need of removing by-products during purification of oligomerization products.

Accordingly, the present inventors have studied various catalyst systems for olefin oligomerization, and found that a catalyst system for olefin oligomerization as described below is used to improve 1-octene selectivity and to produce by-products capable of improving physical properties of polyolefins when 1-octene is used as a comonomer in the preparation of polyolefins, thereby completing the present invention.

DETAILED DESCRIPTION OF THE INVENTION

Technical Problem

The present invention provides a 1-octene composition which is prepared by ethylene oligomerization and comprises a high content of 1-octene and monomers useful for copolymerization of 1-octene at the same time.

Further, the present invention provides a catalyst system for ethylene oligomerization, which is used to prepare the 1-octene composition.

Technical Solution

In order to solve the above objects, the present invention provides a 1-octene composition comprising 90% by weight or more of 1-octene and 0.01 to 10% by weight of three or more of compounds represented by the following Chemical Formulae 1 to 4:

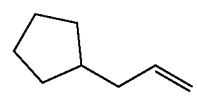

[Chemical Formula 1]

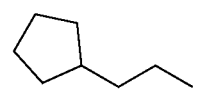

[Chemical Formula 2]

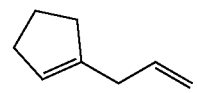

[Chemical Formula 3]

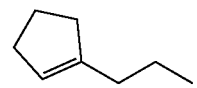

[Chemical Formula 4]

Preferably, the 1-octene composition according to the present invention comprises 0.1 to 1% by weight of three or more of the compounds represented by Chemical Formulae 1 to 4.

The 1-octene composition according to the present invention may be prepared by a method comprising the step of multimerizing ethylene in the presence of a catalyst system for olefin oligomerization, the catalyst system comprising a ligand compound, a transition metal source, and a cocatalyst.

As used herein, the term 'olefin oligomerization' means polymerization of a small number of olefins. When three olefins are polymerized, it is referred to as trimerization. When four olefins are polymerized, it is referred to as tetramerization. The process of polymerizing a small number of olefins to form a low molecular weight material is generally referred to as multimerization. Particularly, in the present invention, the olefin oligomerization means selective preparation of 1-octene, as a main comonomer of LLDPE, from ethylene.

Selective olefin oligomerization is closely related to a catalyst system used. A catalyst system used for olefin oligomerization comprises a transition metal source which functions as a main catalyst, and a cocatalyst, in which the structure of the active catalyst may be changed according to the chemical structure of the ligand, thereby varying olefin selectivity and catalytic activity as well as the kind and content of by-products.

Particularly, in the present invention, the catalyst system for olefin oligomerization described below is used, thereby preparing any one of the compounds represented by Chemical Formulae 1 to 4 as a by-product. Further, a product comprising an alpha-olefin mixture and a solvent, which is prepared by using the catalyst system for olefin oligomerization, may be applied to a proper distillation column to separate a C8 liquid composition having a boiling point of 110 to 140° C. at atmospheric pressure. In particular, the product prepared by using the catalyst system according to the present invention has very high selectivity for 1-octene in the C8 composition, i.e., 90% by weight or more. Preferably, the 1-octene composition according to the present invention comprises 99% by weight or more of 1-octene.

Preferably, the 1-octene composition according to the present invention also comprises all of the compounds represented by Chemical Formulae 1 to 4.

According to an exemplary embodiment of the present invention, the 1-octene composition according to the present invention comprises 99% by weight or more of 1-octene and less than 1% by weight of the compounds represented by Chemical Formulae 1 to 4, and therefore, the composition may have high 1-octene selectivity and comprise by-products useful for polyethylene polymerization.

The ligand compound of the catalyst system for olefin oligomerization comprises two or more of a group represented by the following Chemical Formula 5 in the molecule, in which the two or more of the group are linked via four carbon atoms by a group selected from the group consisting of an aliphatic group having 1 to 20 carbon atoms, an alicyclic group having 3 to 20 carbon atoms, and an aromatic group having 6 to 20 carbon atoms:

[Chemical Formula 5]

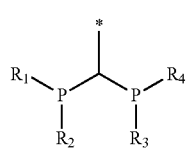

wherein $R_1$ to $R_4$ are each independently $C_{1-20}$ alkyl, $C_{2-20}$ alkenyl, $C_{6-20}$ aryl, $C_{7-20}$ arylalkyl, $C_{7-20}$ alkylaryl, or $C_{7-20}$ alkoxyaryl.

The ligand compound comprises two or more diphosphinoamine functional groups, which are linked to each other via four carbon atoms. A group linking the diphosphinoamine functional groups is a group selected from the group consisting of an aliphatic group having 1 to 20 carbon atoms, an alicyclic group having 3 to 20 carbon atoms, and an aromatic group having 6 to 20 carbon atoms. Due to such structural feature, the ligand compound may exhibit high oligomerization activity when applied to the catalyst system for olefin oligomerization.

Further, there is no theoretical limitation, but a unique interaction occurs between adjacent chromium active sites, due to the structural feature of the ligand compound, leading to partial production of methylenecyclopentane during oligomerization. In turn, this compound is reacted with ethylene to produce the compounds of Chemical Formulae 1 to 4.

Preferably, the group linking the two or more groups via four carbon atoms is selected from the group consisting of the following Chemical Formulae:

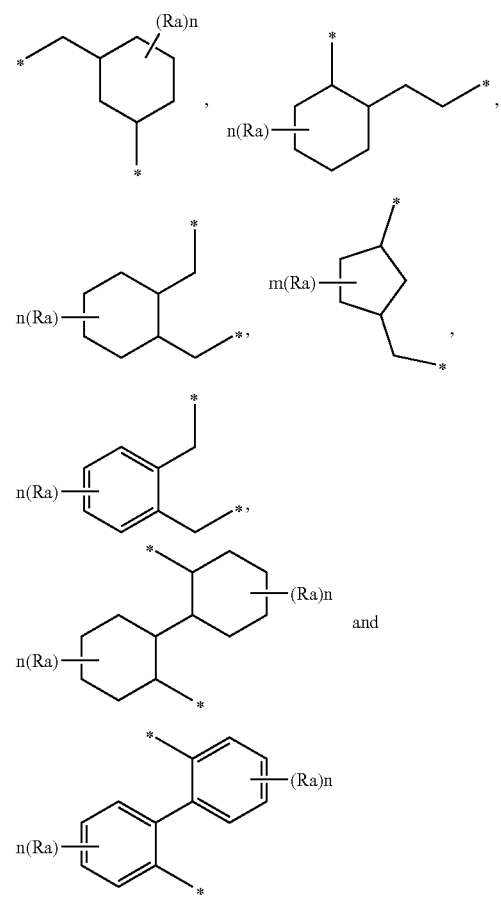

wherein * is a region binding with N of Chemical Formula 1,

Ra is each independently hydrogen, or $C_{1-5}$ alkyl, m is an integer of 1 to 5, n is an integer of 1 to 6, and a plurality of Ra binding to one ring may be the same as or different from each other.

Preferably, $R_1$ to $R_4$ of Chemical Formula 5 are phenyl.

Representative examples of the ligand compound are as follows:

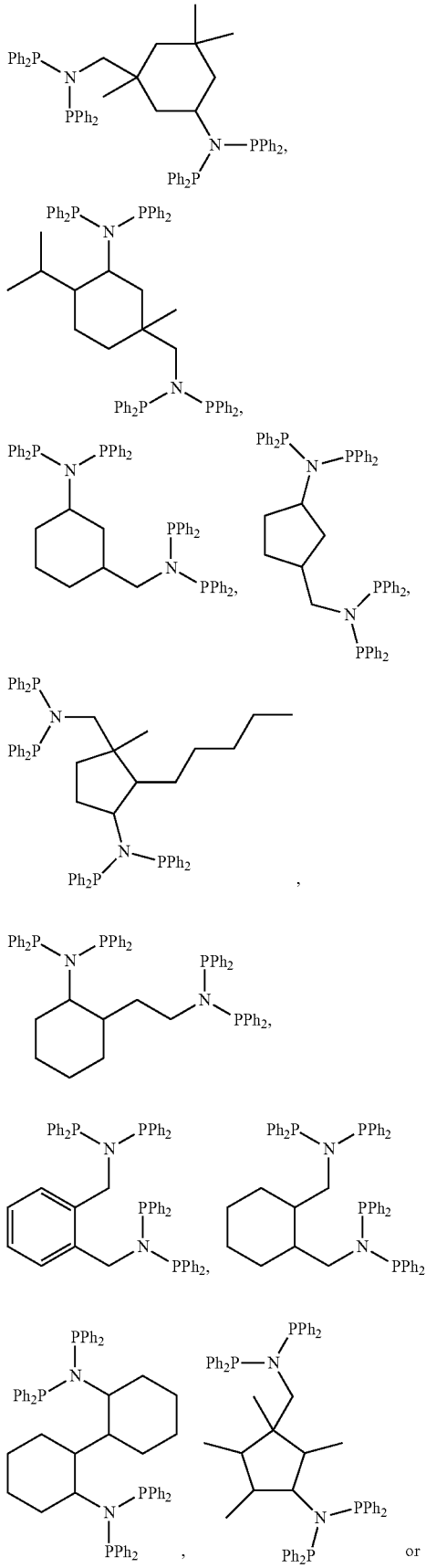

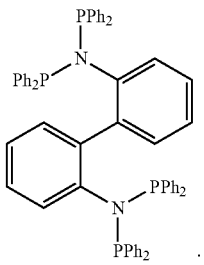

Another example of the ligand compound to achieve the above objects may be a ligand compound represented by the following Chemical Formula 6.

[Chemical Formula 6]

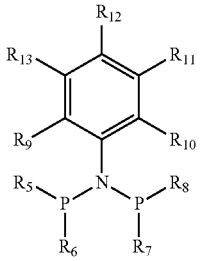

wherein $R_5$ to $R_8$ are each independently $C_{6-20}$ aryl, or $C_{7-20}$ alkylaryl, $R_9$ and $R_{10}$ are each independently $C_{1-20}$ alkyl, with the proviso that $R_9$ and $R_{10}$ are not the same as each other, $R_{11}$ to $R_{13}$ are each independently hydrogen, $C_{1-20}$ alkyl, $C_{2-20}$ alkenyl, $C_{7-20}$ arylalkyl, $C_{7-20}$ arylalkenyl, $C_{3-20}$ cycloalkyl, $C_{3-20}$ cycloalkenyl, $C_{9-20}$ arylcycloalkyl, $C_{9-20}$ arylcycloalkenyl, $C_{6-20}$ aryl, or $C_{7-20}$ alkylaryl.

Preferably, $R_5$ to $R_8$ are phenyl, or 3,5-dimethylphenyl.

Preferably, $R_9$ is methyl, and $R_{10}$ is ethyl.

Preferably, $R_{11}$ to $R_{13}$ are hydrogen.

Representative examples of the compound represented by Chemical Formula 6 are as follows:

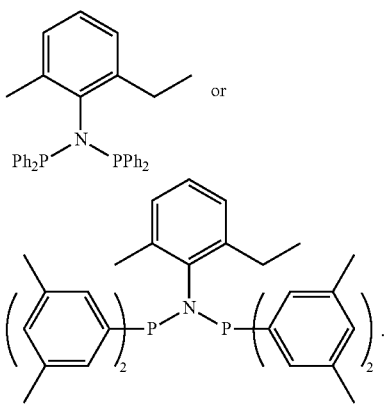

According to an exemplary embodiment of the present invention, when the catalyst system for olefin oligomerization according to the present invention was used to multimerize ethylene, the compounds of Chemical Formulae 1 to 4 were detected in the 1-octene composition as a product.

Further, when 1-octene is used as a comonomer of a polyethylene copolymer, a part of the compounds of Chemical Formulae 1 to 4 may act in copolymerization, together with 1-octene, because they have double bonds at their ends. In general, physical properties of an ethylene/1-octene copolymer may be improved by partially modifying the structure of the polymer through another comonomer, in addition to the comonomer content. Therefore, when the 1-octene composition according to the present invention is used as a monomer of the copolymer, physical properties of the polymer may be improved by the compounds of Chemical Formulae 1 to 4 which are included in the 1-octene composition. On the contrary, internal octenes (e.g., cis and trans isomers of 2-octene, 3-octene, 4-octene) as another type of by-products of the 1-octene composition hardly act in copolymerization due to their steric hindrance.

Meanwhile, in the catalyst system for olefin oligomerization according to the present invention, a transition metal source functions as a main catalyst, and it may be any one or more selected from the group consisting of chromium(III)acetylacetonoate, tris(tetrahydrofuran)chromium trichloride, chromium(III)-2-ethylhexanoate, chromium(III) tris(2,2,6,6-tetramethyl-3,5-heptanedionate), chromium(III) benzoylacetonate, chromium(III)hexafluoro-2,4-pentanedionate, and chromium(III)acetate hydroxide.

Further, in the catalyst system for olefin oligomerization, the cocatalyst may be one or more selected from the group consisting of compounds represented by the following Chemical Formulae 7 to 9:

   [Chemical Formula 7]

wherein $R_{14}$ is the same as or different from each other, and each independently a halogen radical, a hydrocarbyl radical having 1 to 20 carbon atoms, or a halogen-substituted hydrocarbyl radical having 1 to 20 carbon atoms, and c is an integer of 2 or more,

   [Chemical Formula 8]

wherein D is aluminum or boron, and $R_{15}$ is the same as or different from each other, and each independently hydrogen or halogen, a hydrocarbyl having 1 to 20 carbon atoms, or a halogen-substituted hydrocarbyl having 1 to 20 carbon atoms,

   [Chemical Formula 9]

wherein L is a neutral Lewis base, [L-H]$^+$ is a Bronsted acid, Q is boron or aluminium in the +3 oxidation state, and E is each independently an aryl group having 6 to 20 carbon atoms or an alkyl group having 1 to 20 carbon atoms, in which one or more hydrogen atoms are substituted or unsubstituted with halogen, hydrocarbyl having 1 to 20 carbon atoms, an alkoxy functional group or a phenoxy functional group.

Examples of the compound represented by Chemical Formula 7 may include methylaluminoxane (MAO), ethyl aluminoxane, isobutyl aluminoxane, or butyl aluminoxane.

Examples of the compound represented by Chemical Formula 8 may include trimethylaluminium, triethylaluminium, triisobutylaluminium, tripropylaluminium, tributylaluminium, dimethylchloroaluminium, dimethylisobutylaluminium, dimethylethylaluminium, diethylchloroaluminium, triisopropylaluminium, tri-s-butylaluminium, tricyclopentylaluminium, tripentylaluminium, triisopentylaluminium, trihexylaluminium, ethyldimethylaluminium, methyldiethylaluminium, triphenylaluminium, tri-p-tolylaluminium, dimethylaluminiummethoxide, dimethylaluminiumethoxide, trimethylboron, triethylboron, triisobutylboron, tripropylboron, or tributylboron.

Examples of the compound represented by Chemical Formula 9 may include triethylammoniumtetraphenylboron, tributylammoniumtetraphenylboron, trimethylammoniumtetraphenylboron, tripropylammoniumtetraphenylboron, trimethylammoniumtetra(p-tolyl)boron, tripropylammoniumtetra(p-tolyl)boron, triethylammoniumtetra(o,p-dimethylphenyl)boron, trimethylammoniumtetra(o,p-dimethylphenyl)boron, tributylammoniumtetra(p-trifluoromethylphenyl) boron, trimethylammoniumtetra(p-trifluoromethylphenyl) boron, tributylammoniumtetrapentafluorophenylboron, N,N-diethylaniliniumtetraphenyl boron, N,N-diethylaniliniumtetraphenylboron, N,N-diethylaniliniumtetrapentafluorophenylboron, diethylammoniumtetrapentafluorophenylboron, triphenylphosphoniumtetraphenylboron, trimethylphosphoniumtetraphenylboron, triethylammoniumtetraphenylaluminium, tributylammoniumtetraphenylaluminium, trimethylammoniumtetraphenylaluminium, tripropylammoniumtetraphenylaluminium, trimethylammoniumtetra(p-tolyl)aluminium, tripropylammoniumtetra(p-tolyl)aluminium, triethylammoniumtetra(o,p-dimethylphenyl)aluminium, tributylammoniumtetra(p-trifluoromethylphenyl)aluminium, trimethylammoniumtetra(p-trifluoromethylphenyl)aluminium, tributylammoniumtetrapentafluorophenylaluminium, N,N-diethylaniliniumtetraphenylaluminium, N,N-diethylaniliniumtetraphenylaluminium, N,N-diethylaniliniumtetrapentafluorophenylaluminium, diethylammoniumtetrapentafluorophenylaluminium, triphenylphosphoniumtetraphenylaluminium, trimethylphosphoniumtetraphenylaluminium, triphenylcarboniumtetraphenylboron, triphenylcarboniumtetraphenylaluminium, triphenylcarboniumtetra(p-trifluoromethylphenyl)boron or triphenylcarboniumtetrapentafluorophenylboron.

The catalyst system for olefin oligomerization according to the present invention may have a mole ratio of the compound represented by Chemical Formula 5 or 6:transition metal source:cocatalyst of about 1:1:1 to about 10:1:10,000, preferably about 1:1:100 to about 5:1:3,000, so as to increase 1-octene selectivity and multimerization activity. However, the present invention is not limited thereto.

In the catalyst system for olefin oligomerization comprising the compound represented by Chemical Formula 5 or 6, the transition metal source, and the cocatalyst, the three components may be added simultaneously or sequentially in a random order to a suitable solvent in the presence or absence of monomers, and they may be obtained as an active catalyst. The suitable solvent may include heptane, toluene, 1-hexene, diethylether, tetrahydrofuran, acetonitrile, dichloromethane, chloroform, chlorobenzene, methanol, acetone, or the like, but is not limited thereto.

The present invention also provides a method of preparing an olefin oligomer, the method comprising the step of multimerizing olefins in the presence of the catalyst system for olefin oligomerization. When the catalyst system for olefin oligomerization according to the present invention is used, a method of oligomerizing olefin with improved reaction activity and selectivity may be provided. Preferably, the olefin is ethylene.

The olefin oligomerization according to the present invention may be conducted as a homogeneous liquid phase reaction, a slurry reaction, in which a catalyst system is not dissolved in part or in whole, a two-phase liquid/liquid reaction, or a bulk phase reaction or a gas phase reaction, in which a product olefin acts as a main medium, in the presence or absence of an inert solvent, using the catalyst system for olefin oligomerization and a common device and contact technology. The homogeneous liquid phase reaction is preferred.

The olefin oligomerization may be conducted in any inert solvent that does not react with a catalyst compound and an activator. The suitable inert solvent may include benzene, toluene, xylene, cumene, heptane, cyclohexane, methylcyclohexane, methylcyclopentane, hexane, pentane, butane, isobutane, or the like, but is not limited thereto. In this regard, the solvent may be treated with a small amount of alkylaluminum to remove a small amount of water or air acting as a catalyst poison, before use.

The olefin oligomerization may be conducted at a temperature of about 5° C. to about 200° C., preferably about 30° C. to about 150° C. Further, the olefin oligomerization may be conducted at a pressure of about 1 bar to about 300 bar, preferably about 2 bar to about 150 bar.

Advantageous Effects

A 1-octene composition according to the present invention is prepared by ethylene oligomerization and comprises a high content of 1-octene and monomers useful for copolymerization of 1-octene at the same time.

BRIEF DESCRIPTION OF DRAWINGS

FIG. 1 shows the result of analyzing an octene composition prepared in an exemplary embodiment of the present invention.

DETAILED DESCRIPTION OF THE EMBODIMENTS

Hereinafter, the present invention will be explained in more detail with reference to the following Examples. However, these Examples are only to illustrate the invention, and the scope of the invention is not limited thereto.

Hereinafter, all the reactions were progressed using a Schlenk technique or a Glove box under an argon atmosphere. The synthesized compounds were analyzed by $^1H$ (500 MHz) and $^{31}P$ (202 MHz) NMR spectra using a Varian 500 MHz spectrometer. Shift was expressed in ppm, downfield from TMS, with a residual solvent peak as a reference. A phosphorous probe was calibrated with aqueous $H_3PO_4$.

PREPARATION EXAMPLE 1

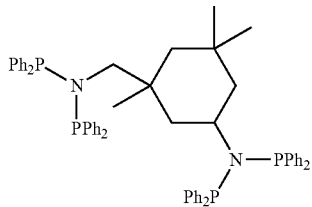

Under an argon atmosphere, 3-(aminomethyl)-3,5,5-trimethylcyclohexaneamine (5 mmol) and triethylamine (3-10 equivalents) were dissolved in dichloromethane (80 mL). While the flask was immersed in a water bath, chlorodiphenylphosphine (20 mmol) was slowly added, and the mixture was stirred overnight. The solvent was removed under vacuum, and then THF was added, the mixture was sufficiently stirred, and triethylammonium chloride salt was removed with an air-free glass filter. The solvent was removed from the filtrate to obtain a target compound.

$^{31}P$ NMR (202 MHz, $CDCl_3$): 45.6 (br s), 56.2 (br s)

PREPARATION EXAMPLE 2

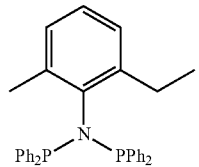

Under an argon atmosphere, 2-ethyl-6-methylaniline (10 mmol) and triethylamine (3 equivalents) were dissolved in dichloromethane (80 mL). While the flask was immersed in a water bath, chlorodiphenylphosphine (20 mmol) was slowly added, and the mixture was stirred overnight. The solvent was removed under vacuum, and then THF was added, the mixture was sufficiently stirred, and triethylammonium chloride salt was removed with an air-free glass filter. The solvent was removed from the filtrate to obtain a target compound.

$^{31}P$ NMR (202 MHz, $CDCl_3$): 59.2 (br s)

PREPARATION EXAMPLE 3

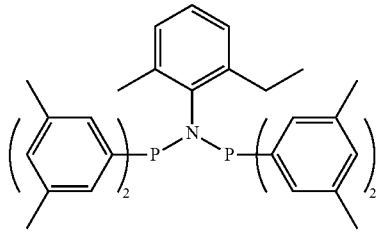

Under an argon atmosphere, 2-ethyl-6-methylaniline (10 mmol) and triethylamine (3 equivalents) were dissolved in dichloromethane (80 mL). While the flask was immersed in a water bath, chlorobis(3,5-dimethylphenyl)phosphine (20 mmol) was slowly added, and the mixture was stirred overnight. The solvent was removed under vacuum, and then THF was added, the mixture was sufficiently stirred, and triethylammonium chloride salt was removed with an air-free glass filter. The solvent was removed from the filtrate to obtain a target compound.

$^{31}P$ NMR (202 MHz, $CDCl_3$): 57.2 (br s)

EXAMPLE 1

Step 1

Under argon gas, $Cr(acac)_3$ (17.5 mg, 0.05 mmol) and the compound prepared in Preparation Example 1 (0.025 mmol) were added into a flask, methylcyclohexane (100 mL) was added, and the mixture was stirred to prepare a 0.5 mM solution (based on Cr).

Step 2

Vacuum was applied to 600 mL-Parr reactor for 2 hours at 120° C., then the internal atmosphere was replaced with argon, and the temperature was lowered to 60° C. 175 mL of methylcyclohexane and 2 mL of MMAO (isoheptane solution, Al/Cr=1200) were added, and 5 mL of 0.5 mM solution (2.5 umol) was added into the reactor. The mixture was stirred at 500 rpm for 1 minute, a valve of an ethylene line adjusted to 60 bar was opened to fill the inside of the reactor with ethylene, and then the temperature was controlled to 60° C. and the mixture was stirred at 500 rpm for 15 minutes. The ethylene line valve then was closed, the reactor was cooled to 0° C. with a dry ice/acetone bath, non-reacted ethylene was slowly vented, and 0.5 mL of nonane (GC internal standard) was added. After stirring for 10 seconds, 2 mL of the liquid part of the reactor was taken and quenched with water, and the organic part was filtered with a PTFE syringe filter to make a sample. The sample was analyzed by GC-MS and GC-FID as in the following Experimental Example, and quantified by GC-FID.

Step 3

400 mL of ethanol/HCl (10 vol %) was added to the remaining reaction solution, and the mixture was stirred and filtered to obtain a polymer. The obtained polymer was dried overnight in a vacuum oven at 65° C., and the weight was measured.

EXAMPLE 2

The same process as in Example 1 was conducted to prepare a sample and a polymer, except that the compound prepared in Preparation Example 2 (0.05 mmol) was used instead of the compound prepared in Preparation Example 1.

EXAMPLE 3

The same process as in Example 1 was conducted to prepare a sample and a polymer, except that the compound prepared in Preparation Example 3 (0.05 mmol) was used instead of the compound prepared in Preparation Example 1.

EXAMPLE 4

The same process as in Example 1 was conducted to prepare a sample and a polymer, except that the compound prepared in Preparation Example 2 (0.05 mmol) was used instead of the compound prepared in Preparation Example 1 and n-heptane was used instead of methylcyclohexane as a solvent.

COMPARATIVE EXAMPLE 1

1-Octene (98%, 04806-1L) purchased from Sigma-Aldrich was used as Comparative Example 1.

COMPARATIVE EXAMPLE 2

1-Octene purchased from INEOS was used as Comparative Example 2.

COMPARATIVE EXAMPLE 3

The same process as in Example 1 was conducted to prepare a sample and a polymer, except that a catalyst system prepared from $Cr(acac)_3$, $Ph_2PN(iPr)PPh_2$ and MMAO according to the literature (J. Am. Chem. Soc. 2005, 127, 10723-10730) was used.

EXPERIMENTAL EXAMPLE

GC-FID analysis was conducted using 1-octene compositions of Examples and Comparative Examples as follows.

AT-5 column (0.32 mm ID×30 mL) was used, and gases such as Column (He) 1.6 mL/min, Make-up (He) 30 mL/min, Hydrogen 40 mL/min, and Air 400 mL/min were applied and analyzed. During analysis, the program was as follows: the temperature of an oven was maintained at 35° C. for 5 minutes, and then raised at a rate of 1° C./min. At a moment when the temperature reached 50° C., the temperature was raised at a rate of 15° C./min. The temperature was maintained at 300° C. for 30 minutes and then terminated. Analysis was conducted at an injector temperature of 270° C., at a detector temperature of 280° C., and at an injector split of 25/1 with an injection volume of 0.2 uL.

The analysis results are given in the following Table 1, together with the catalytic activity.

TABLE 1

| | Catalytic activity (ton/molCr/hr) | 1-Hexene (wt %) | 1-Octene (wt %) | 1-Hexene + 1-octene (wt %) | C6 isomers (wt %) |
|---|---|---|---|---|---|
| Ex. 1 | 196 | 39.0 | 45.3 | 84.3 | 3.6 |
| Ex. 2 | 161 | 49.5 | 40.5 | 90.0 | 1.5 |
| Ex. 3 | 156 | 39.2 | 52.6 | 91.9 | 1.0 |
| Ex. 4 | 131 | 24.1 | 63.2 | 87.3 | 2.0 |

The C8 compositions or the compositions of by-products in Examples 1 to 4 and Comparative Examples 1 to 3 are given in the following Table 2, in which the by-products appeared around 1-octene peak expected to have a boiling point of 110° C. to 140° C. under atmospheric pressure.

Further, GC chromatogram of Example 1 is shown in FIG. 1.

TABLE 2

| # | Products in C8 composition | GC-FID elution time (min) | Ex. 1 (wt %) | Ex. 2 (wt %) | Ex. 3 (wt %) | Ex. 4 (wt %) | Com. Ex. 1 | Com. Ex. 2 | Com. Ex. 3 |
|---|---|---|---|---|---|---|---|---|---|
| 1 | 1-Octene | 8.25-8.65 | 99.012 | 99.267 | 99.349 | 99.244 | >98 wt % | 85.7 wt % | — |
| 2 | n-Octane | 8.699 | 0.122 | 0.016 | 0.022 | 0.000 | ○[2)] | ○ | ○ |
| 3 | 2-Octene | 8.824 | 0.104 | 0.059 | 0.048 | 0.120 | ○ | ○ | ○ |
| 4 | 2-Octene | 8.942 | 0.026 | 0.019 | 0.035 | 0.000 | ○ | ○ | ○ |
| 5 | Chemical Formula 1 | 9.186 | 0.218 | 0.153 | 0.229 | 0.094 | X[3)] | X | ○ |
| 6 | Chemical Formula 2 | 9.637 | 0.113 | 0.078 | 0.123 | 0.045 | X | X | ○ |

TABLE 2-continued

| # | Products in C8 composition | GC-FID elution time (min) | Ex. 1 (wt %) | Ex. 2 (wt %) | Ex. 3 (wt %) | Ex. 4 (wt %) | Com. Ex. 1 | Com. Ex. 2 | Com. Ex. 3 |
|---|---|---|---|---|---|---|---|---|---|
| 7 | Chemical Formula 3 | 10.063 | 0.231 | 0.221 | 0.114 | 0.266 | X | X | X |
| 8 | Chemical Formula 4 | 10.589 | 0.174 | 0.187 | 0.079 | 0.232 | Trace | X | X |
|  | 1 + 2 + 3 + 4[1] |  | 0.736 | 0.639 | 0.545 | 0.637 |  |  |  |
|  | Sum |  | 100 | 100 | 100 | 100 |  |  |  |

[1]Sum of Chemical Formulae 1 to 4
[2]detected
[3]undetected

The invention claimed is:

1. A polyethylene copolymer copolymerized with ethylene monomer and unsaturated C8 comonomers,
wherein the unsaturated C8 comonomers comprise
a) 90% by weight or more, based on the total weight of the unsaturated C8 comonomers, of 1-octene, and
b) 0.01 to 10% by weight, based on the total weight of the unsaturated C8 comonomers, of three compounds represented by the following Chemical Formulae 1, 3, and 4:

[Chemical Formula 1]

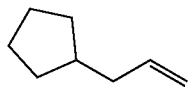

[Chemical Formula 3]

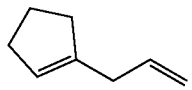

[Chemical Formula 4]

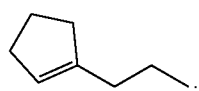

2. The polyethylene copolymer of claim 1,
wherein the unsaturated C8 comonomers comprise 0.1 to 1% by weight, based on the total weight of the unsaturated C8 comonomers, of three or more of the compounds represented by Chemical Formulae 1, 3, and 4.

3. The polyethylene copolymer of claim 1,
wherein the unsaturated C8 comonomers comprise 99% by weight or more, based on the total weight of the unsaturated C8 comonomers, of 1-octene.

4. The polyethylene copolymer of claim 1,
wherein the unsaturated C8 comonomers comprise all of the compounds represented by Chemical Formulae 1, 3, and 4.

* * * * *